United States Patent [19]

Dürckheimer et al.

[11] 3,947,449

[45] Mar. 30, 1976

[54] TETRAHYDROACRIDONES HAVING CHEMOTHERAPEUTIC ACTION AND PROCESS FOR PREPARING THEM

[75] Inventors: Walter Dürckheimer, Hattersheim, Main; Wolfgang Raether, Dreieichenhain; Hubert Georg Seliger, Frankfurt am Main, all of Germany

[73] Assignee: Hoechst Aktiengesellschaft, Frankfurt am Main, Germany

[22] Filed: July 22, 1974

[21] Appl. No.: 490,652

[30] Foreign Application Priority Data

July 24, 1973 Germany............................ 2337474

[52] U.S. Cl.......... 260/279 R; 260/586 R; 260/599; 424/257
[51] Int. Cl.²................. C07D 219/06; A61K 31/47

[58] Field of Search .................................. 260/279 R

[56] References Cited
OTHER PUBLICATIONS

Sivaswami et al., Current Science, (India), No. 6, June, 1950, p. 180.
Albert, "The Acridines", 2nd ed., St. Martin's Press, N.Y., 1966, pp. 133–135.

Primary Examiner—Richard J. Gallagher
Assistant Examiner—Diana G. Rivers
Attorney, Agent, or Firm—Curtis, Morris & Safford

[57] ABSTRACT

Tetrahydroacridones and their salts with physiologically tolerated acids and bases and process for preparing them. The compounds have a valuable chemotherapeutic action and may be used as drugs against protozoan diseases.

16 Claims, No Drawings

TETRAHYDROACRIDONES HAVING CHEMOTHERAPEUTIC ACTION AND PROCESS FOR PREPARING THEM

The present invention provides tetrahydroacridones of the general formula I and their salts with physiologically tolerated acids and bases

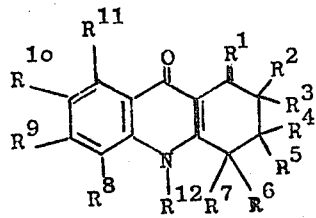

(I)

in which
R$^1$ represents oxygen or the hydrazone radical =N—NH$_2$,
R$^2$ to R$^7$, which may be identical or different, represent hydrogen, a straight or branched, saturated or unsaturated lower alkyl radical, a phenyl group which may be substituted once, twice or thrice by fluorine, chlorine, bromine, iodine, trifluoromethyl, nitro, cyano, carbamyl, sulfamyl, acetyl, lower alkyl-sulfoxy and phenyl-sulfoxy, lower alkyl-sulfonyl and phenyl-sulfonyl, lower alkoxy, or methylene-dioxy, with the limitation that only one of the radicals R$^2$ to R$^7$ represents an aromatic radical,
R$^8$ to R$^{11}$, which may be identical or different, represent hydrogen, fluorine, chlorine, bromine, iodine, trifluoromethyl, cyano, lower alkyl, lower alkoxy,
R$^{12}$ represents hydrogen, a hydroxyl group, or a straight or branched lower acyloxy group.

The term "lower" used hereinbefore and hereinafter with reference to radicals denotes such radicals which contain 1 to 6 carbon atoms, preferably radicals which contain 1 to 4 carbon atoms.

The invention also relates to a process for preparing the compounds of the formula I, which comprises reacting the compounds of the formulae II and III

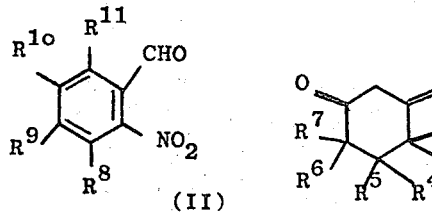

(II)     (III)

in which the radicals R$^2$ to R$^{11}$ have the meanings given above, in a water-miscible organic solvent and in the presence of a mineral acid, preferably concentrated hydrochloric or hydrobromic acid, at a temperature in the range of from 20 to 120° C, preferably 80° to 100° C, to form a compound of the formula IV

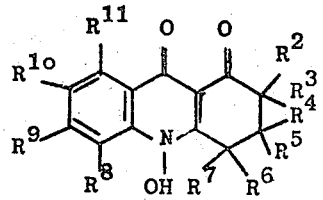

(IV)

and, if R$^1$ in formula I represents a hydrazone radical, condensing this compound with hydrazine,
or, if R$^{12}$ in formula I represents hydrogen, reducing this compound with phosphorus trichloride,
or, if R$^{12}$ in formula I represents a straight or branched lower acyloxy group, reacting this compound with an acid halide or acid anhydride of the formula V or VI $$R^{13}—COCl \qquad V$$

$$R^{13}—CO—O—CO—R^{13} \qquad VI.$$

in which R$^{13}$ represents a straight or branched lower alkyl radical.

The 2-nitrobenzaldehydes of the formula II used as starting substances are obtained starting from toluene derivatives which are nitrated in 2-position, halogenated in the methyl group and which are subsequently converted into the aldehydes of the formula II according to the method of F. Krohnke (Ber. 69, 2006 (1936)). The following compounds are cited by way of example as starting materials:

2-nitrobenzaldehyde, 3-chloro-2-nitrobenzaldehyde, 4-chloro-2-nitrobenzaldehyde, 6-chloro-2-nitrobenzaldehyde, 4-fluoro-2-nitrobenzaldehyde, 5-fluoro-2-nitrobenzaldehyde, 4-bromo-2-nitrobenzaldehyde, 4-trifluoromethyl-2-nitrobenzaldehyde, 5-trifluoromethyl-2-nitrobenzaldehyde, 6-trifluoromethyl-2-nitrobenzaldehyde, 4-methoxy-2-nitro-benzaldehyde, 5-ethoxy-2-nitrobenzaldehyde, 4-butoxy-2-nitrobenzaldehyde, 3-methyl-2-nitrobenzaldehyde, 4-hexyl-2-nitrobenzaldehyde.

The 1,3-cyclohexane-dione derivatives of the formula III are obtained either by catalytic hydrogenation of correspondingly substituted resorcinal derivatives in the presence of bases (Organikum, 4th Edition, 1964, page 257), or by cyclization reactions as those described, for example, for dimedone (Org. Synth. Coll. Vol. II, page 200), 5-o-chlorophenyl-1,3-cyclohexanedione (L. H. Hinkel, E. E. Ayling, J. F. J. Dippy, J. Chem. Soc., London, 1935, page 539) and 4-hydroxyphenyl-1,3-cyclohexanedione (Ph. E. Papadakis, J. Am. Chem. Soc. 67, page 1799, (1945)).

As examples, there may be mentioned: 1,3-cyclohexane-dione, 4-methyl-1,3-cyclohexane-dione, 4-ethyl-1,3-cyclohexane-dione, 4-tert.-butyl-1,3-cyclohexane-dione, 4-phenyl-1,3-cyclohexane-dione, 4-(4-chlorophenyl)-1,3-cyclohexane-dione, 4-(4-fluorophenyl)-1,3-cyclohexane-dione, 4-(3,4-dichlorophenyl)-1,3-cyclohexane-dione, 4-(4-trifluoromethylphenyl)-1,3-cyclohexane-dione, 5-methyl-1,3-cyclohexane-dione, 5-ethyl-1,3-cyclohexane-dione, 5-propyl-1,3-cyclohexane-dione, 5-iso-propyl-1,3-cyclohexanedione, 5-butyl-1,3-cyclohexane-dione, 5-hexyl-1,3-cyclohexanedione, 5-(2-hydroxyethyl)-1,3-cyclohexane-dione, 5-cyclopentyl-1,3-cyclohexane-dione, 5-cyclohexyl-1,3-cyclohexane-dione, 5-(3-hydroxypropyl)-1,3-cyclohexane-dione, 5-phenyl-1,3-cyclohexanedione, 5-p-chlorophenyl-1,3-cyclohexane-dione, 5-p-fluorophenyl-1,3-cyclohexane-dione, 5-p-bromophenyl-1,3-cyclohexane-dione, 5-p-trifluoromethylphenyl-1,3-cyclohexane-dione, 5-p-methoxyphenyl-1,3-cyclohexane-dione, 5-p-tolyl-1,3-cyclohexane-dione, 5-p-cyanophenyl-1,3-cyclohexane-dione, 5-p-sulfamylphenyl-1,3-cyclohexane-dione, 5-(4-methylsulfonyl-phenyl)-1,3-cyclohexanedione, 5-(4-carbamylphenyl)-

1,3-cyclohexane-dione, 5-(4-iodophenyl)-1,3-cyclohexane-dione, 5-(4-acetylphenyll)-1,3-cyclohexane-dione, 5-(4-phenoxyphenyl)-1,3-cyclohexane-dione, 5-(3,4-methylenedioxyphenyl)-1,3-cyclohexane-dione, 5-(3-chlorophenyl)-1,3-cyclohexane-dione, 5-(3-fluorophenyl)-1,3-cyclohexane-dione, 5-(3-bromophenyl)-1,3-cyclohexane-dione, 5-(3-trifluorophenyl)-1,3-cyclohexane-dione, 5-(3-cyanophenyl)-1,3-cyclohexane-dione, 5-(3-sulfonylmethylphenyl)-1,3-cyclohexane-dione, 5-m-nitrophenyl-1,3-cyclohexane-dione, 5-(3-sulfamylphenyl)-1,3-cyclohexane-dione, 5-(3-methylsulfoxyphenyl)-1,3-cyclohexane-dione, 5-(3-ethoxyphenyl)-1,3-cyclohexane-dione, 5-(2-fluorophenyl)-1,3-cyclohexane-dione, 5-(2-chlorophenyl)-1,3-cyclohexane-dione, 5-(2-trifluoromethylphenyl)-1,3-cyclohexane-dione, 5-(2-bromophenyl)-1,3-cyclohexane-dione, 5(2-tolyl)-1,3-cyclohexane-dione, 5-(2-cyanophenyl)-1,3-cyclohexanedione, 5-(2-acetylphenyl)-1,3-cyclohexane-dione, 5-(2,3-dichlorophenyl)-1,3-cyclohexane-dione, 5-(2,4-dichlorophenyl)-1,3-cyclohexane-dione, 5-(2,5-dichlorophenyl)-1,3-cyclohexane-dione, 5-(3,4-dichlorophenyl)-1,3-cyclohexane-dione, 5-(2-chloro-4-fluorophenyl)-1,3-cyclohexane-dione, 5-(3-chloro-4-fluorophenyl)-1,3-cyclohexane-dione, 5-(2-chloro-4-trifluoromethylphenyl)-1,3-cyclohexane-dione, 5-(3-chloro-4-trifluoromethylphenyl)-1,3-cyclohexane-dione, 5-(2-bromo-5-trifluoromethylphenyl)-1,3-cyclohexane-dione, 5-(2-chloro-4-iodophenyl)-1,3-cyclohexane-dione, 5-(3-methyl-4-fluorophenyl)-1,3-cyclohexane-dione, 5-(2-methoxy-4-chlorophenyl)-1,3-cyclohexanedione, 5-(2-chloro-4-cyanophenyl)-1,3-cyclohexane-dione, 5-(2-methyl-5-trifluoromethylphenyl)-1,3-cyclohexane-dione, 5-(3-chloro-5-sulfonylmethylphenyl-1,3-cyclohexane-dione, 5-(2-chloro-6-methoxyphenyl)-1,3-cyclohexane-dione, 5-(3-chloro-4-butylphenyl)-1,3-cyclohexane-dione, 5-(2-chloro-4-sulfonylphenyl)-1,3-cyclohexane-dione, 5-(2-ethyl-5-sulfonylmethylphenyl)-1,3-cyclohexane-dione, 4,4-dimethyl-1,3-cyclohexane-dione, 5,5-dimethyl-1,3-cyclohexane-dione, 4,6-dimethyl-1,3-cyclohexane-dione, 4-methyl-6-ethyl-1,3-cyclohexane-dione, 4-tert.-butyl-6-methyl-1,3-cyclohexane-dione, 5,5-diethyl-1,3-cyclohexane-dione, 5-methyl-5-phenyl-1,3-cyclohexane-dione, 5-methyl-5-p-chlorophenyl-1,3-cyclohexane-dione, 5-methyl-5-p-fluorophenyl-1,3-cyclohexanedione, 5-methyl-5-p-trifluorophenyl-1,3-cyclohexane-dione, 4-methyl-5-p-chlorophenyl-1,3-cyclohexane-dione, 4,6-dimethyl-5-p-chlorophenyl-1,3-cyclohexane-dione, 4-methyl-5-(3,4-dichlorophenyl)-1,3-cyclohexane-dione, 5-methyl-5-(m-methylsulfonylphenyl)-1,3-cyclohexane-dione, 4-methyl-5-(m-fluorophenyl)-1,3-cyclohexane-dione.

The compounds of the formula IV are prepared preferably by heating one mole of an aldehyde of the formula II and one mole of a cyclohexanedione of the formula III in a mixture of glacial acetic acid and concentrated hydrochloric acid for 1 to 2 hours to 80° – 100° C and subsequently precipitating the reaction product by the addition of water. The quantity of glacial acetic acid depends on the solubility of the starting components and can be varied within wide limits. Instead of glacial acetic acid, also other water-miscible solvents such as formic acid, propionic acid, tetrahydrofurane, dioxane, glycol dimethyl ether, glycol monomethyl ether, alcohols, etc. are suitable.

The quantity of hydrochloric acid, too, can be varied within wide limits, but should not be lower than 1 mole because the yields would then decrease. The aqueous hydrochloric acid can be replaced by gaseous hydrogen chloride which may be introduced into the reaction solution.

The reaction temperature depends on the reactivity and stability of the components. With well soluble starting substances, heating is not absolutely necessary. It is sufficient to allow the reaction mixture to stand for several days, if necessary up to one week, at room temperature and then to concentrate or to precipitate with water.

A peculiarity of the reaction consists in the fact that when using 2-nitrobenzaldehydes which are unsubstituted in the 5-position, a chlorine atom is introduced into the 7-position of the reaction product (substituent $R^{10}$). If, instead of hydrochloric acid, concentrated hydrobromic acid, hydrogen bromide gas or hydrogen bromide/glacial acetic acid is used, a bromine atom can be introduced at the same place. If, however, the 5-position of the 2-nitrobenzaldehyde is already substituted, for example by chlorine, bromine, fluorine or alkoxy, and if no further halogen atom is to be introduced, it is of advantage to add to the batch at least one mole of a reducing agent, for example hydroquinone, pyrogallol, oxyhydroquinone or ascorbic acid.

The compounds of the formula IV can be converted into a monohydrazone by heating with an excess (2 to 20 moles) of an aqueous hydrazine solution. The sparingly soluble hydrazone is first treated with acid, for example hydrochloric acid, sulfuric acid, acetic acid, or phosphoric acid, in order to separate the excess of hydrazine and the aqueous suspension of the hydrazone salt so obtained is then combined with a base until the pH-value of the solution is between 7 and 8.

When heated with acid anhydrides which when used in excess simultaneously serve as solvent, the compounds of the formula IV react to monoacyl derivatives. These compounds crystallize directly or may be obtained after destruction of the excess anhydride. Instead of the acid anhydrides, acid halides may also be used for the acylation, for example acetyl chloride, chloroacetyl chloride, propionic acid chloride or butyric acid bromide.

The tetrahydroacridones of the formula I prepared according to the invention constitute colorless to weakly yellow crystalline compounds which are sparingly soluble in water and in most of the organic solvents at room temperature and which in most cases melt at temperatures above 200° C with decomposition.

They can be recrystallized from polar solvents, for example formic acid, glacial acetic acid, dimethylformamide, glycol monomethyl ether. Because of their amphoteric nature, they form salts with acids and bases. Thus, for example, the hydrochlorides or hydrobromides which hydrolyze easily in water can be prepared with hydrochloric acid or hydrobromic acid in alcohols. The salts of sulfuric acid show a similar behaviour.

The salts with bases are more soluble in water than the free compounds. They are obtained, for example by dissovling 1 mole of tetrahydroacridone of the formula IV with 1 mole of a strong base in water or alcohols and carefully concentrating this solution or lyophilizing it. When working in alcohols, they may also be precipitated by the addition of non-polar solvents, for example ether or ethyl acetate. As bases, there may be used all strong bases the cations of which are physiologically tolerated, for example sodium hydroxide, potassium hydroxide, calcium hydroxide or tetramethylammonium hydroxide.

The compounds of the formula I prepared according to the invention constitute a novel class of chemical compounds and are valuable chemotherapeutic agents which are particularly suitable for the control of infections by protozoa. They are distinguished, for example by a high activity against the pathogens of malaria, especially against such strains which do not sufficiently respond to the conventional drugs, for example chloroquin and related compounds. The number of therapy resistant cases has considerably increased in the malaria infested areas of the world. Therefore, there is an urgent need for novel antimalarial drugs which have no crossresistance to known drugs.

Furthermore, the compounds of the invention are also active against the pathogens of coccidiosis (for example, coccidiosis of fowl, turkeys, rabbits, cattle and pigs).

In the present day mass management of animals for slaughter, coccidiosis is a real problem during the rearing and fattening period, because it may cause considerable economical losses. Therefore, the availability of highly active, well tolerated coccidiostatics is of highest interest.

The compounds of the formula I may be administered perorally or parenterally in doses ranging from 2.5 to 100 mg/kg of body weight. As antimalarial drugs, dosage unit forms such as dragees or capsules for oral administration or solutions and suspensions, respectively, for injections, each containing 100 to 400 mg of active substance are preferred. Such dosage units are administered once to three times daily depending on the condition of the patient.

For oral administration, there may be used in particular tablets, dragees, capsules, powders or granules which contain the active substances together with the usual excipients and adjuvants such as starch, cellulose powder, talcum, magnesium stearate, sugar, gelatin, calcium carbonate, finely divided silicic acid, carboxymethyl-cellulose or similar substances.

For parenteral administration, in particular for intramuscular injections, there may be used sterile suspensions, for example oily suspensions prepared with the use of sesame oil, castor oil or synthetic triglycerides, optionally with simultaneous use of surface-active substances such as sorbitan fatty acid esters. Furthermore, there may also be used aqueous suspensions prepared, for example with the use of ethoxylated sorbitan fatty acid esters, optionally with addition of thickeners such as polyethylene glycol or carboxymethyl-cellulose.

In addition, the compounds of the formula I may also be administered in admixture with suitable feedstuffs.

For use as veterinary drugs, the concentration of the active substances of the invention in the preparations produced with them is preferably in the range of from 2 and 30 % by weight; for use as medicaments for humans, the concentration of the active substances is preferably in the range of from 20 to 80 % by weight.

The compounds of the formula I may also be used in combination with other active substances.

The following examples illustrate the invention.

EXAMPLES:

A 1: 7-Chloro-3-(2-chloro-4-trifluoromethylphenyl)-10-hydroxy-1-oxo-1,2,3,4-tetrahydro-9(10H)-acridone 15.1 g (0.1 mole) of 2-nitrobenzaldehyde and 29 g (0.1 mole) of 5-(2-chloro-4-trifluoromethylphenyl)-1,3-cyclohexane-dione were heated, while stirring, for 1 hour, to 80° C, in a mixture of 100 ml of glacial acetic acid and 100 ml of concentrated hydrochloric acid. The reaction solution was poured into 1.5 liters of water, the precipitate that had formed was filtered off and washed with water until it was free from chlorine ions. The still wet filter cake was boiled with 500 ml of methanol for 20 minutes under reflux and with stirring, filtered off again and washed with methanol and ether. After drying, 32.4 g of the above-specified compound were obtained (73.2 % of yield); decomposition point 260° C.

$C_{20}H_{12}Cl_2F_3NO_3$ (442.2); Calc.: C 54.3; H 2.75; N 3.15; Cl 16.0 %; Found: C 54.0; H 3.1; N 3.2; Cl 16.0 %.

In analogous manner, there were obtained from the correspondingly substituted 2-nitrobenzaldehydes and 1,3-cyclohexanediones the following compounds:

A 2: 7-chloro-10-hydroxy-1-oxo-3-phenyl-1,2,3,4,tetrahydro-9(10H)-acridone
Decomposition point: 245°–250°C A 3: 7-chloro-3-(4-chlorophenyl)-10-hydroxy-1-oxo-1,2,3,4-tetrahydro-9(10H)-acridone
Decomposition point from 270°C onwards A 4: 7-chloro-3-(2-chlorophenyl)-10-hydroxy-1-oxo-1,2,3,4-tetrahydro-9 (10H)-acridone
Decomposition point from 238° to 243°C A 5: 7-bromo-3-(4-chlorophenyl)-10-hydroxy-1-oxo-1,2,3,4-tetrahydro-9 (10H)-acridone A 6: 7-chloro-10-hydroxy-1-oxo-3-(4-trifluoromethylphenyl)-1,2,3,4-tetrahydro-9 (10H)-acridone
Decomposition point from 330°C onwards A 7: 7-fluoro-10-hydroxy-1-oxo-3-(4-trifluoromethylphenyl)-1,2,3,4-tetrahydro-9 (10H)-acridone A 8: 7-fluoro-10-hydroxy-1-oxo-3-(4-chlorophenyl)-1,2,3,4-tetrahydro-9 (10H)-acridone A 9: 7-fluoro-10-hydroxy-1-oxo-3-(4-fluorophenyl)-1,2,3,4-tetrahydro-9 (10H)-acridone A 10: 7-chloro-3-(2,4-dichlorophenyl)-10-hydroxy-1-oxo-1,2,3,4-tetrahydro-9 (10H)-acridone
Decomposition point from 283° to 285°C A 11: 7-chloro-3-(3-chlorophenyl)-10-hydroxy-1-oxo-1,2,3,4-tetrahydro-9 (10H)-acridone
Decomposition point from 248° to 250°C A 12: 7-chloro-3-(4-fluorophenyl)-10-hydroxy-1-oxo-1,2,3,4-tetrahydro-9 (10H)-acridone
Decomposition point from 257° to 258°C A 13: 7-chloro-10-hydroxy-1-oxo-3-(2-trifluoromethylphenyl)-1,2,3,4-tetrahydro-9 (10H)-acridone
Decompositon point 260°C A 14: 7-chloro-3-(2,6-dichlorophenyl)-10-hydroxy-1-oxo-1,2,3,4-tetrahydro-9 (10H)-acridone
Decomposition point from 239° to 240°C A 15: 6-chloro-10-hydroxy-1-oxo-3-(4-trifluoromethylphenyl)-1,2,3,4-tetrahydro-9 (10H)-acridone A 16: 7-chloro-(3,4-dichlorophenyl)-10-hydroxy-1-oxo-1,2,3,4-tetrahydro-9 (10H)-acridone
Decomposition point 275°C A 17: 5-fluoro-3-(4-fluorophenyl)-10-hydroxy-1-oxo-1,2,3,4-tetrahydro-9 (10H)-acridone A 18: 7-chloro-10-hydroxy-3-(4-nitrophenyl)-1-oxo-1,2,3,4-tetrahydro-9 (10H)-acridone
Decomposition point from 340°C onwards A 19: 7-chloro-10-hydroxy-3-(3,4-methylenedioxyphenyl)-1-oxo-1,2,3,4-tetrahydro-9 (10H)-acridone
Decomposition point 245°C A 20: 7-chloro-10-hydroxy-3-(4-methoxyphenyl)-1-oxo-1,2,3,4-tetrahydro-9 (10H)-acridone Decomposition point from 268° to 270°C A 21: 7-chloro-10-hydroxy-3-(2-methoxyphenyl)-1-oxo-1,2,3,4-tetrahydro-9 (10H)-acridone Decomposition point from 205° to 210°C A 22: 6-chloro-3-(4-chlorophenyl)-10-hydroxy-1-oxo-1,2,3,4-tetrahydro-9 (10H)-acridone A 23: 7-chloro-10-hydroxy-3-i-propyl-1-oxo-1,2,3,4-tetrahydro-9 (10H)-acridone Decomposition point from 251° to 252°C A 24: 7-chloro-10-hydroxy-2-methyl-1-oxo-1,2,3,4-tetrahydro-9 (10H)-acridone Decomposition point from 240°C onwards A 25: 7-chloro-2,2-dimethyl-10-hydroxy-1-oxo-1,2,3,4-tetrahydro-9 (10H)-acridone Decomposition point from 234° to 235° C A 26: 7-chloro-2,4-di-tert.-butyl-10-hydroxy-1-oxo-1,2,3,4-tetrahydro-9 (10H)-acridone Decomposition point from 248 to 249°C A 27: 7-chloro-10-hydroxy-1-oxo-2-tert. butyl-1,2,3,4-tetrahydro-9 (10H)-acridone Decomposition point from 220° to 222°C A 28: 6,7-dichloro-10-hydroxy-1-oxo-3-(4-chlorophenyl)-1,2,3,4-tetrahydro-9 (10H)-acridone A 29: 6,7-dichloro-10-hydroxy-1-oxo-3-(3-trifluoromethylphenyl)-1,2,3,4-tetrahydro-9 (10H)-acridone A 30: 3,3-dimethyl-7-fluoro-10-hydroxy-1-oxo-1,2,3,4-tetrahydro-9 (10H)-acridone A 31: 3-n-butyl-7-fluoro-10-hydroxy-1-oxo-1,2,3,4-tetrahydro-9 (10H)-acridone A 32: 7-chloro-10-hydroxy-6-methoxy-1-oxo-1,2,3,4-tetrahydro-9 (10H)-acridone A 33: 7-n-butoxy-3-(4-fluorophenyl)-10-hydroxy-1-oxo-1,2,3,4-tetrahydro-9 (10H)-acridone A 34: 7-chloro-3-(4-chlorophenyl)-10-hydroxy-5-methyl-1-oxo-1,2,3,4-tetrahydro-9 (10H)-acridone A 35: 7-chloro-10-hydroxy-1-oxo-3-(4-sulfamylphenyl)-1,2,3,4-tetrahydro-9 (10H)-acridone A 36: 7-chloro-3-(4-cyanophenyl)-10-hydroxy-1-oxo-1,2,3,4-tetrahydro-9 (10H)-acridone A 37: 7-chloro-3-(4-chloro-3-hexylphenyl)-10-hydroxy-1-oxo-1,2,3,4-tetrahydro-9 (10H)-acridone A 38: 6,7-dichloro-3,3-dimethyl-10-hydroxy-1-oxo-1,2,3,4-tetrahydro-9 (10H)-acridone Decomposition point from 251° to 254°C A 39: 7-chloro-3,3-dimethyl-10-hydroxy-1-oxo-1,2,3,4-tetrahydro-9(10H)-acridone Decomposition point 236°C A 40: 7-bromo-3,3-dimethyl-10-hydroxy-1-oxo-1,2,3,4-tetrahydro-9(10H)-acridone Decomposition point 230°C A 41: 7-chloro-3,3-dimethyl-10-hydroxy-6-methoxy-1-oxo-1,2,3,4-tetrahydro-9(10H)-acridone Decomposition point 277°C A 42: 3,3-dimethyl-10-hydroxy-7-methoxy-1-oxo-1,2,3,4-tetrahydro-9(10H)-acridone Decomposition point from 233° to 235°C A 43: 3,3-dimethyl-7-fluoro-10-hydroxy-1-oxo-1,2,3,4-tetrahydro-9(10H)-acridone Decomposition point from 208° to 210°C A 44: 7-chloro-2-(4-chlorophenyl)-10-hydroxy-1-oxo-1,2,3,4-tetrahydro-9(10H)-acridone A 45: 7-chloro-2-(4-fluorophenyl)-10-hydroxy-1-oxo-1,2,3,4-tetrahydro-9(10H)-acridone B 1: 3,3-Dimethyl-10-hydroxy-1-oxo-1,2,3,4-tetrahydro-9(10H)-acridone 15.1 g (0.1 mole) of 2-nitrobenzaldehyde, 14.1 g (0.1 mole) of dimedone and 22 g (0.2 mole) of hydroquinone were dissolved in 200 ml of glacial acetic acid. Hydrogen chloride gas was vigourously introduced during 3 hours at 80° to 90° C, the whole was allowed to stand overnight and the glacial acetic acid was removed under reduced pressure. The crystalline residue (25 g) yielded upon dissolution and recrystallization from 125 ml of ethanol 19.5 g of 3,3-dimethyl-10-hydroxy-1-oxo-1,2,3,4-tetrahydro-9(10H)-acridone hydrochloride. The compound was dissolved in water whereupon the free base precipitated after a short time. After recrystallization from methanol, there were obtained 15 g (58 % of the theory) of the above-specified compound which had a decomposition point from 200° to 202° C.

$C_{15}H_{15}NO_3$ (257.3); Calc.: C 70.0; H 5.9; N 5.4 %; Found: C 69.8; H 5.8; N 5.3 %.

In analogous manner, there were obtained with the use of the correspondingly substituted 2-nitrobenzaldehydes and 1,3-cyclohexane-diones the following compounds:

B 2: 8-chloro-3,3-dimethyl-10-hydroxy-1-oxo-1,2,3,4-tetrahydro-9 (10H)-acridone-hydrochloride Decomposition point from 198° to 200°C B 3: 8-chloro-3,3-dimethyl-10-hydroxy-1-oxo-1,2,3,4-tetrahydro-9 (10H)-acridone Decomposition point 293°C B 4: 10-hydroxy-1-oxo-1,2,3,4-tetrahydro-9 (10H)-acridone Decomposition point from 203° to 205°C B 5: 6-chloro-3,3-dimethyl-10-hydroxy-1-oxo-1,2,3,4-tetrahydro-9 (10H)-acridone Decomposition point from 209° to 210°C B 6: 3,3-dimethyl-10-hydroxy-6-methoxy-1-oxo-1,2,3,4-tetrahydro-9 (10H)-acridone Decomposition point 250°C B 7: 3-n-hexyl-10-hydroxy-6-fluoro-1-oxo-1,2,3,4-tetrahydro-9 (10H)-acridone B 8: 2-n-butyl-10-hydroxy-1-oxo-1,2,3,4-tetrahydro-9 (10H)-acridone B 9: 6,8-dichloro-2,4-dimethyl-10-hydroxy-1-oxo-1,2,3,4-tetrahydro-9 (10H)-acridone B 10: 6-fluoro-3-(4-fluorophenyl)-10-hydroxy-1-oxo-1,2,3,4-tetrahydro-9 (10)-acridone C 1: 7,8-Dichloro-3,3-dimethyl-10-hydroxy-1-oxo-1,2,3,4-tetrahydro-9(10H)-acridone 18.6 g (0.1 mole) of 6-chloro-2-nitrobenzaldehyde and 14 g (0.1 mole) of dimedone were dissolved in 260 ml of glacial acetic acid and a strong stream of hydrogen chloride gas was introduced at 80° C. After about 6 hours, the whole was heated under reflux and HCl gas was introduced for further 4 hours. The solution was filtered until clear, concentrated under reduced pressure, the residue was triturated with 50 ml of methanol and allowed to stand overnight in a refrigerator. After separation by suction-filtration and dissolution and recrystallization from a mixture of glacial acetic acid and water, there were obtained 2.7 g (8 %) of the above-specified compound having a decomposition point of 272° C.

$C_{15}H_{13}Cl_2NO_3$ (326.2); Calc: C 55.2; H 4.0; N 4.3 %; Found: C 55.2; H 4.1; N 4.6 %.

C 2: 3-(4-Chlorophenyl)-7,8-dichloro-10-hydroxy-1oxo-1,2,3,4-tetrahydro-9(10H)-acridone D 1: 7-Chloro-10-hydroxy-3-methyl-1-oxo-1,2,3,4-tetrahydro-9(10H)-acridone 30.2 g (0.2 mole) of 2-nitrobezaldehyde and 25.2 g (0.2 mole) of 5-methyl-1,3-cyclohexane-dione were dissolved in 300 ml of tetrahydrofurane, the solution was saturated at 18° C with hydrogen chloride and allowed to stand for 4 days at room temperature. Water was added, the oily layer was separated and stirred with methanol. The crystals that had formed were filtered off, washed with methanol and dissolved and recrystallized from glacial acetic acid. 9.5 g (17 % of the theory) of 7-chloro-3-methyl-10-hydroxy-1-oxo-1,2,3,4-tetrahydro-9(10H)-acridone having a decomposition point of 255° C were obtained.

The compound was obtained with a higher yield when using the reaction conditions described in Example A 1.

$C_{14}H_{12}ClNO_3$ (277.7); Calc.: C 60.5; H 4.4; N 5.0; Cl 12.8 %; Found: C 61.1; H 4.5; N 5.1; Cl 12.8 %.

In analogous manner, there were obtained from 2-nitrobenzaldehyde and correspondingly substituted 1,3-cyclohexanediones the following compounds:

D 2: 7-Chloro-3-n-propyl-10-hydroxy-1oxo-1,2,3,4-tetrahydro-9(10H)-acridone

D 3: 2-i.-Butyl-7-chloro-10-hydroxy-1oxo-1,2,3,4-tetrahydro-9(10H)-acridone

E 1: 7-Chloro-3,3-dimethyl-1-oxo-1,2,3,4-tetrahydro-9(10H)-acridone 20 g (0.066 mole) of 7-chloro-3,3-dimethyl-10-hydroxy-1-oxo-1,2,3,4-tetrahydro-9(10H)-acridone were suspended in 320 ml of chloroform and, after heating on a steam bath, combined dropwise with 11.3 ml (0.13 mole) of phosphorus trichloride. Upon cooling, 16 g of 7-chloro-3,3-dimethyl-1-oxo-1,2,3,4-tetrahydro-9(10H)-acridone crystallized in the form of the hydrochloride. This compound was dissolved in a mixture of 300 ml of methanol and 50 ml of binormal sodium hydroxide solution, the solution was filtered, the filtrate was concentrated under reduced pressure and the base that had crystallized was filtered off with suction. 13.5 g (74 %) of 7-chloro-3,3-dimethyl-1-oxo-1,2,3,4-tetrahydro-9(10H)-acridone were obtained. Decomposition point 300° C.

$C_{15}H_{14}ClNO_2$ (275.7); Calc.: C 65.4; H 5.1; N 5.1; Cl 12.9 %; Found: C 65.6; H 5.2; N 5.8; Cl 12.5 %.

F 1: 10-Acetoxy-7-chloro-3,3-dimethyl-1-oxo-1,2,3,4-tetrahydro-9(10H)-acridone 29.1 g (0.1 mole) of 7-chloro-3,3-dimethyl-10-hydroxy-1-oxo-1,2,3,4-tetrahydro-9(10H)-acridone were heated with 100 ml of acetanhydride for 90 minutes on the steam bath. Upon cooling, 17.5 g of the above-specified compound crystallized directly; further 1.9 g were obtained upon concentration of the mother liquor. Decomposition point 207° C.

$C_{17}H_{16}ClNO_4$ (333.8); Calc.: C 61.2; H 4.8; N 4.2; Cl 10.6 %; Found: C 61.1; H 4.7; N 4.5; Cl 10.9 %.

G 1: 7-Chloro-3,3-dimethyl-1-hydrazono-10-hydroxy-1,2,3,4-tetrahydro-9(10H)-acridone 16.4 g (0.05 mole) of 7-chloro-3,3-dimethyl-10-hydroxy-1-oxo-1,2,3,4-tetrahydro-9(10H)-acridone were boiled for 90 minutes under reflux in a mixture of 30 ml of hydrazine hydrate (80% strength) and 150 ml of water. The precipitate was filtered off with suction, washed with water and treated with 150 ml of concentrated hydrochloric acid. A hydrochloride was formed which was filtered off after addition of a small amount of water. For conversion into the free base, the hydrochloride was suspended in 300 ml of water and binormal sodium hydroxide solution was added until the pH-value was 8. After suction-filtration, washing with water and drying, 13 g (85 %) of 7-chloro-3,3-dimethyl-1-hydrazono-10-hydroxy-1,2,3,4-tetrahydro-9(10H)-acridone were obtained which was found to decompose from 160° C onwards.

$C_{15}H_{16}ClN_3O_2$ (305.8); Calc.: C 58.9; H 5.3; N 13.7; Cl 11.6 %; Found: C 57.6; H 5.5; N 13.5; Cl 11.9 %.

We claim:

1. A tetrahydroacridone of the formula

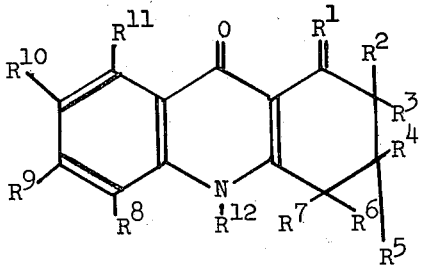

and salts thereof with physiologically tolerated acids and bases, wherein $R^1$ is oxygen; $R^2 - R^7$, which may be the same or different are hydrogen, straight-chain or branched lower alkyl having 1 to 4 carbon atoms, phenyl, or phenyl mono- or di-substituted with fluorine, chlorine, or trifluoromethyl, except that only one of $R^2 - R^7$ is phenyl or substituted phenyl; $R^8$, $R^9$, and $R^{11}$, which may be the same or different, are hydrogen, fluorine, chlorine, or trifluoromethyl; $R^{10}$ is chlorine; and $R^{12}$ is hydrogen or hydroxy.

2. 7-chloro-3-(2-chloro-4-trifluoromethylphenyl)-10-hydroxy-1-oxo-1,2,3,4-tetrahydro-9 (10H)-acridone.

3. 7-chloro-10-hydroxy-1-oxo-3-phenyl-1,2,3,4-tetrahydro-9 (10H)-acridone.

4. 7-chloro-3-(4-chlorophenyl)-10-hydroxy-1-oxo-1,2,3,4-tetrahydro-9 (10H)-acridone.

5. 7-chloro-3-(2-chlorophenyl)-10-hydroxy-1-oxo-1,2,3,4-tetrahydro-9 (10H)-acridone.

6. 7-chloro-10-hydroxy-1-oxo-3-(4-trifluoromethylphenyl)-1,2,3,4-tetrahydro-9 (10H)-acridone.

7. 7-chloro-3-(2,4-dichlorophenyl)-10-hydroxy-1-oxo-1,2,3,4-tetrahydro-9 (10H)-acridone.

8. 7-chloro-3-(3-chlorophenyl)-10-hydroxy-1-oxo-1,2,3,4-tetrahydro-9 (10H)-acridone.

9. 7-chloro-3-(4-fluorophenyl)-10-hydroxy-1-oxo-1,2,3,4-tetrahydro-9 (10H)-acridone.

10. 7-chloro-10-hydroxy-3-(4-nitrophenyl)-1-oxo-1,2,3,4-tetrahydro-9 (10H)-acridone.

11. 7-chloro-10-hydroxy-3-(2-methoxyphenyl)-1-oxo-1,2,3,4-tetrahydro-9 (10H)-acridone.

12. 6,7-dichloro-10-hydroxy-1-oxo-3-(3-trifluorophenyl)-1,2,3,4-tetrahydro-9 (10H)-acridone.

13. A method for making a tetrahydroacridone of the formula

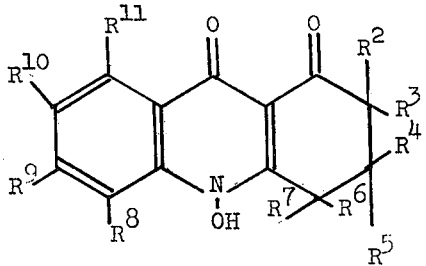

wherein $R^2 - R^7$, which may be the same or different, are hydrogen, straight-chain or branched lower alkyl having 1 to 4 carbon atoms, phenyl, nitrophenyl, lower alkoxy phenyl having 1 to 4 carbon atoms in the alkoxy, methylenedioxy phenyl, sulfamyl phenyl, or phenyl mono- or di-substituted with fluoro, chloro, or trifluoromethyl, except that only one of $R^2 - R^7$ is phenyl or substituted phenyl; and $R^8 - R^{11}$, which may be the same or different, are hydrogen, fluorine, chlorine, bromine, lower alkyl having 1 to 4 carbon atoms, lower alkoxy having 1 to 4 carbon atoms, or trifluoromethyl, except that $R^{10}$ is other than hydrogen; which comprises reacting a compound of the formula

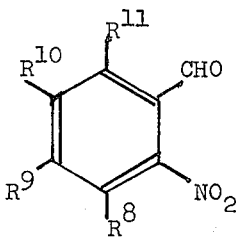

with a compound of the formula

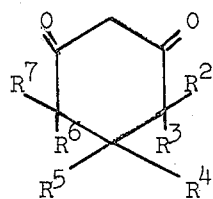

in a water-miscible solvent and in the presence of a mineral acid.

14. A method as in claim 13 wherein said tetrahydroacridone is subsequently reacted with hydrazine to replace the 1-oxygen atom by 1-hydrazono.

15. A method as in claim 13 wherein said tetrahydroacridone is subsequently reacted with phosphorus trichloride to reduce the 10-hydroxy group to hydrogen.

16. A method as in claim 13 wherein said tetrahydroacridone is subsequently reacted with an acid chloride or acid anhydride of the formula $R^{13}$—COCl or $R^{13}$—CO—O—CO—$R^{13}$, wherein $R^{13}$ is lower alkyl having 1 to 4 carbon atoms, to esterify the 10-hydroxy group.

* * * * *